(12) United States Patent
Pike et al.

(10) Patent No.: US 6,630,019 B2
(45) Date of Patent: Oct. 7, 2003

(54) CALCIUM PHOSPHATE COLORANTS AND METHOD FOR MAKING SAME

(75) Inventors: Kathleen S. Pike, Bel Air, MD (US); John A. Kostinko, Bel Air, MD (US)

(73) Assignee: J. M. Huber Corporation, Edison, NJ (US)

( * ) Notice: Subject to any disclaimer, the term of this patent is extended or adjusted under 35 U.S.C. 154(b) by 24 days.

(21) Appl. No.: 09/944,970

(22) Filed: Aug. 31, 2001

(65) Prior Publication Data

US 2003/0129149 A1 Jul. 10, 2003

(51) Int. Cl.[7] .............................................. C09B 63/00
(52) U.S. Cl. ...................... 106/462; 106/467; 106/471; 424/49; 426/250; 426/540; 427/215; 427/218; 428/403
(58) Field of Search ................................. 106/462, 467, 106/471; 428/403; 427/215, 218; 426/250, 540; 424/49

(56) References Cited

U.S. PATENT DOCUMENTS

| | | | |
|---|---|---|---|
| 4,084,983 | | 4/1978 | Bernhard et al. ........... 106/289 |
| 5,127,952 | * | 7/1992 | Persello et al. ............. 106/492 |
| 5,318,628 | | 6/1994 | Matijevic et al. ........... 106/499 |
| 5,855,869 | | 1/1999 | Domke et al. ................ 424/49 |
| 6,143,280 | | 11/2000 | Pike et al. .................... 424/49 |

FOREIGN PATENT DOCUMENTS

| | | | | |
|---|---|---|---|---|
| JP | 09-328623 | * | 12/1997 | ........... C09B/63/00 |

* cited by examiner

Primary Examiner—C. Melissa Koslow
Assistant Examiner—Shalie Manlove
(74) Attorney, Agent, or Firm—Carlos Nieves; David M. Goodrich

(57) ABSTRACT

Calcium phosphate colorants are provided that comprise calcium phosphate particles, a dye, and aluminum hydroxide and which are resistant to dye migration and suitable for use in food, drugs and cosmetics. The calcium phosphate particles are coated with a dye and the dye is fixed to the particles by the aluminum hydroxide. Also provided is a method for making a calcium phosphate colorant in which aluminum hydroxide is mixed with a calcium phosphate slurry to deposit aluminum hydroxide onto the calcium phosphate particles contained within the slurry.

30 Claims, No Drawings

CALCIUM PHOSPHATE COLORANTS AND METHOD FOR MAKING SAME

BACKGROUND OF THE INVENTION

Colorants are used in most consumer products to provide a distinctive and pleasing appearance. Food and personal care products use almost exclusively two kinds of colorants: Food, Drug and Cosmetic ("FD&C") dyes and Drug and Cosmetic ("D&C") dyes, because both kinds of these dyes are non-toxic. In addition to their non-toxicity, these dyes have the additional benefit of being water-soluble, and so when admixed into an aqueous consumer product they are homogeneously distributed throughout the bulk of the product to give it a uniform color.

However, these dyes may not be suitable for use in a multi-colored consumer product. Multi-colored consumer products are those that have two or more regions of contrasting color and/or consistency. Examples of multicolored products are toothpastes that are transparent or white and contain small speckles, as well as toothpastes made from two or more layers, each having its own distinctive color.

While multi-colored consumer products may be more attractive to consumers, they pose difficulties in formulation and manufacture. In particular, such products are susceptible to the effects of dye migration between the differently colored regions. "Dye migration" in this sense refers to the tendency of a dye in a multilayered product to migrate from one region of a product into an adjacent region of a product. Such migration occurs by the physical process of diffusion and is also known as "bleeding". This migration or bleeding is undesirable because it compromises the distinctive appearance of the consumer product and prevents the product formulator from predictably controlling the aesthetics of the product.

One way to prevent dye migration is to physically separate the differently colored regions until actual use. For example, toothpaste containers have been developed for storing multi-layered toothpastes that maintain each of the layers in a separate compartment until the layers are combined as a single toothpaste product upon dispensing from the container. While this mechanical approach to the problem of dye migration is effective, such containers are expensive and increase the cost of the product.

Using alternative colorants instead of FD&C and D&C dyes may provide a chemical solution to the problem of dye migration that is considerably less expensive than the aforementioned mechanical solution. Colored pigments, which are finely powdered, water-insoluble materials that are dispersed and suspended in a consumer product are one possible alternative to the water-soluble dyes. Indeed, because they are water-insoluble these pigments are highly resistant to dye migration in aqueous compositions.

Unfortunately, most conventional colored pigments are not suitable for use in food or personal care products because of concerns relating to their toxicity. But these toxicity concerns may be managed by substituting "lake pigments" for conventional pigments. Lake pigments are colorants formed by reacting an organic dye with aluminum or calcium salt on a water-insoluble inorganic substrate. The most commonly used substrate is alumina. Lake pigments can be manufactured to be non-toxic and suitable for use in food, drugs and personal care products. However, while lake pigments are more resistant to dye migration than FD&C and D&C dyes, they still exhibit an unacceptably high level of dye migration.

Given the foregoing, there is a continuing need to develop non-toxic colorants that are both non-toxic and highly resistant to dye migration so as to make them suitable as colorant additives in multi-colored consumer products.

BRIEF SUMMARY OF THE INVENTION

The invention includes a method of forming a calcium phosphate colorant. A first step of this method is providing a calcium phosphate slurry comprising calcium phosphate particles. Aluminum hydroxide is mixed with the calcium phosphate slurry to form a premix, thereby depositing aluminum hydroxide onto the calcium phosphate particles. Thereafter, a dye is added to the calcium phosphate particles having been treated with aluminum hydroxide, wherein the dye is fixed to the calcium phosphate particles by the aluminum hydroxide.

The invention also includes a calcium phosphate colorant resistant to dye migration and comprising calcium phosphate particles, a dye, and aluminum hydroxide.

Preferred dyes include FD&C and D&C dyes.

DETAILED DESCRIPTION OF THE INVENTION

All parts, percentages and ratios used herein are expressed by weight unless otherwise specified. All documents cited herein are incorporated by reference.

The following describes preferred embodiments of the present invention, which provides calcium phosphate colorants as well as a process for making such colorants. These colorants are suitable for use in cosmetic, food, and oral care products having excellent resistance to dye migration and being non-toxic.

By "mixture" it is meant any combination of two or more substances, in the form of, for example without intending to be limiting, a heterogeneous mixture, a suspension, a solution, a sol, a gel, a dispersion, or an emulsion.

By "coated" it is meant that the specified coating ingredient covers at least a portion of the outer surface of a particle or substrate.

By "slurry" it is meant an aqueous mixture of water and at least one other component, wherein water forms the continuous phase.

By "cosmetic product" it is meant any product applied directly to an external or internal part of the body, for example without intending to be limiting, make-up, eye shadow, foundations, lipstick, nail polish, aftershaves, facial creams, shower gels, toothpastes, clown make-up, novelty Halloween costume creams and make-up, sensory perception agents, shaving cream, shampoos, bar soaps, liquid soaps, detergents, foot powders, anti-perspirants and deodorants, eye liners, body glitter, theatrical make-up, body paints, and moisturizers.

By "dentifrices" it is meant oral care products such as, without intending to be limiting, toothpastes, tooth powders and denture creams.

By "food product" it is meant any product meant to be consumed, as well as additives to food products such as, without intending to be limiting, food colorants, anti-caking and free flow agents.

By "dye" it is meant an organic colorant, derived from coal tar and petroleum-based intermediates.

By "colorant" it is meant any substance that imparts color to another material or mixture.

By "lake pigment" it is meant a colorant made by extending on an alumina substrate, a salt prepared from water-soluble straight colors by combining such color with the basic radical aluminum or calcium.

By "F&DC dyes" and "D&C dyes" it is meant any dye listed in Title 21, part 82 of the Code of Federal Regulations, the content of which is hereby incorporated by reference.

By "fixing" is meant to hold a dye permanently on a substrate by chemical or mechanical action, or a combination of both.

The ingredients of the calcium phosphate colorant as well as a method for making the colorant will now be discussed in detail. Subsequently, products that comprise the calcium phosphate colorant will be discussed and examples of such products provided.

The present calcium phosphate colorant contains calcium phosphate, aluminum hydroxide and a dye.

The calcium phosphate is present as particles and these particles may be formed from a variety of suitable calcium phosphate species such as monocalcium phosphate, also known as monobasic calcium phosphate, acid calcium phosphate, calcium biphosphate, primary calcium phosphate and $CaH_4(PO_4)_2$; dicalcium phosphate, also known as dibasic calcium phosphate, calcium monohydrogen phosphate, secondary calcium phosphate and $CaHPO_4$; dicalcium phosphate dihydrate, $CaHPO_4 \cdot 2H_2O$; tricalcium phosphate, which is also referred to by the following names: tribasic calcium phosphate, tertiary calcium phosphate, bone ash, TCP and $Ca_3(PO_4)_2$; calcium pyrophosphate, also referred to as calcium diphosphate and $Ca_2P_2O_7$. Preferred calcium phosphate species are tricalcium phosphate, $Ca_3(PO_4)_2$, dicalcium phosphate, $CaHPO_4$, and calcium pyrophosphate. The properties of these preferred calcium phosphate species are as follows:

TABLE I

|  | Dicalcium phosphate dihydrate | Calcium Pyrophosphate | Tricalcium phosphate |
|---|---|---|---|
| BET, $m^2/g$ | 5 | 10 | 67 |
| Oil absorption, ml/100 g | 26 | 38 | 82 |
| Mean particle size, $\mu m$ | 17 | 12.3 | 6.6 |
| Median particle size, $\mu m$ | 15.0 | 7.6 | 5.0 |
| Hg Pore Volume, ml/g | 0.94 | 1.44 | 2.87 |

In Table I, oil absorption was determined by the rub-out method of ASTM-D281. The pore volume was determined by mercury intrusion porosimetry using a micromeritics AutoPore II 9220 unit. Pore voumes were determined over an intrusion pressure range of 10.0 to 6,029 psi. Data were collected using an advancing contact angle of 130 degrees and a pressure equilibration time of 10 seconds per intrusion measurement point. The BET surface area was determined by the BET nitrogen absoprtion method of Brunaur et al., as reported in the J. Am. Chem. Soc. 60, 309 (1938). The particle size measures were made using a Leeds and Northrup Microtrac II apparatus. All of these tests are described in greater detail in U.S. Pat. No. 6,171,384, issued Jan. 9, 2001 to Conley et al.

The calcium phosphate particles are coated with aluminum hydroxide and dye. Methods for preparing the aluminum hydroxide are discussed below. Any water-soluble, non-toxic dye capable of forming a lake pigment can be used, while Food, Drug & Cosmetic (FD&C) or Drug and Cosmetic (D&C) dyes are preferred. Multiple dyes can be blended together so that by mixing together dyes of different colors a wide variety of colors can be obtained. For example, a green dye can be produced by mixing together blue and yellow dyes.

The process to combine the aforementioned ingredients to form a calcium phosphate colorant will now be discussed in greater detail.

First, a calcium phosphate slurry containing calcium phosphate particles is prepared. Next, the calcium phosphate is "treated" with aluminum hydroxide. The aluminum hydroxide, preferably in the form of a gel, may be prepared in advance and is deposited onto the calcium phosphate particles by mixing the aluminum hydroxide with the calcium phosphate slurry in a reactor or mixing vessel. Because it is desired to maintain a low concentration of $Na_2SO_4$ in the aluminum hydroxide, and because the conductivity of the aluminum hydroxide is proportional to the $Na_2SO_4$ concentration, the conductivity of the aluminum hydroxide gel should be adjusted to be less than 5000 $\mu$mhos. If desired, instead of adjusting the conductivity of the aluminum hydroxide gel, the conductivity of the mixture of the calcium phosphate and aluminum hydroxide may be adjusted in the reactor vessel instead.

Alternatively, instead of preparing the aluminum hydroxide in advance, the aluminum hydroxide may be prepared in situ in the reaction vessel. The in situ method proceeds as follows. An aqueous solution of aluminum sulfate is first added to a reactor or mixing vessel, before any other chemical compounds. Then an aqueous solution of a base, preferably sodium carbonate, is added to the vessel and mixed with the aqueous solution of aluminum sulfate. The aluminum sulfate and base react to produce aluminum hydroxide according to the following reaction:

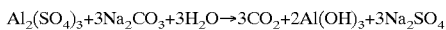
$$Al_2(SO_4)_3 + 3Na_2CO_3 + 3H_2O \rightarrow 3CO_2 + 2Al(OH)_3 + 3Na_2SO_4$$

Calcium phosphate slurry (comprising calcium phosphate particles) is then added to the vessel and mixed together under agitation with the aluminum hydroxide, so that the calcium phosphate particles are coated with aluminum hydroxide. The resulting slurry is filtered and washed to remove by-product sodium sulfate and the wetcake thereby obtained is reslurried.

Subsequently, the calcium phosphate slurry prepared by either of the above described methods, or in fact any other suitable method, is colored by the addition of one or more dyes. The slurry of colored calcium phosphate is then filtered and dried at a temperature $T_1$, to obtain a colored calcium phosphate having a moisture level $M_1$; preferably $M_1$ is less than about 10%, by weight. Conventional oven or spray-drying techniques are suitable. The colored calcium phosphate is then washed and filtered to remove excess dye, which continues until a colorless filtrate is obtained. The filtrate is considered colorless when it has an absorption of less than 0.1 at the wavelength that is characteristic of the dye as determined by UV/Visible spectrometry.

After the excess dye is removed, the wetcake produced by the combination of washing and filtering is dried at a temperature $T_2$, to form a calcium phosphate colorant having a moisture level $M_2$. It is important that the second calcium phosphate cake should never be dried to a moisture level lower than the moisture level of the first calcium phosphate cake (i.e., $M_2 \geq M_1$), and it is equally important that the temperature at which the second calcium phosphate cake is dried should always be less than the drying temperature of the first calcium phosphate cake (i.e., $T_1 \geq T_2$).

This calcium phosphate colorant is a lake pigment with the dye or dyes being "fixed" to the aluminum hydroxide coated calcium phosphate particles. Because of this fixing, the dyes strongly adhere to the particles and are therefore highly resistant against separating from the particles and contributing to dye migration Having been formed from the aforementioned ingredients and by the aforementioned process steps, the present calcium phosphate colorants may be used in a variety of different consumer products, such as cosmetic products, dentrifices and food products. Specifically, if the calcium phosphate colorant is to be used as the colorant in a layer of a striped toothpaste (as discussed in greater detail below), then after drying the colorant should be preferably milled to a powder, i.e. to a median particle size of less than 25 μm and preferably from about 5 μm to about 15 μm (as measured with a Horiba particle size analyzer). If the colorant is used instead to form speckles in a toothpaste formulation, it is compacted into granules and the granules screened to a size of about 600 μm to about 180 μm.

The invention will now be described in more detail with respect to the following, specific, non-limiting examples.

EXAMPLES 1–4

In Examples 1–4, calcium phosphate colorants were prepared according to the present invention. First, aluminum hydroxide gel was prepared by placing 1600 g of a 12% aqueous solution of aluminum sulfate into a vessel, and then adding 18% aqueous solution of sodium carbonate to the vessel at a rate of rate of 14 ml/minute until the pH reached 5.9. The reactants were mixed for 20 minutes with agitation. The resultant aluminum hydroxide slurry was vacuum filtered on a Buchner funnel utilizing Whatman #4 filter paper. The mother liquor (filtrate) was retained for later conductivity adjustment. Next, the aluminum hydroxide gel was washed with 1 liter of water, pulled dry with vacuum then reslurried with 1 liter of water. The retained mother liquor was then added to the slurry and mixed for 30 minutes to adjust the conductivity of the slurry to 1500 μmhos, and the slurry thereafter filtered to form an aluminum hydroxide gel.

Next, 54 grams of dicalcium phosphate dihydrate was slurried with 400 g of water and then 200 g of aluminum hydroxide gel prepared above was reslurried in 100 ml of water and added to the dicalcium phosphate dihydrate slurry at a rate of 15 ml/min. The slurry was mixed for 15 minutes with agitation and the resultant product recovered by filtration to form a wetcake. This wetcake was then re-slurried with 150 g of water and combined with an aqueous dye solution, and mixed together for approximately 1 hour to form a slurry of colored calcium phosphate. For the slurry of Example No. 1, the aqueous dye solution was 200 ml of a 1% FD&C Blue No. 1 aqueous solution. The aqueous dye solution of Example 2 was 200 ml of 1% aqueous solution of FD&C Blue #2; for Example 3 it was 200 ml of 0.75% aqueous red solution (1.29 g FD&C red #33 and 0.21 g FD&C red #40); and for Example 4 the aqueous dye solution was 40 ml of a 2% aqueous solution FD&C yellow #5 and 160 ml of a 1% aqueous solution of FD&C Blue #1 to form a green aqueous dye solution.

Each of the colored calcium phosphate slurries prepared according to Examples 1–4 was then filtered and oven dried at 105° C. overnight to produce a dried cake of calcium phosphate. The cake was then milled, re-slurried in 1000 ml of water, and filtered and washed to remove excess dye until a colorless filtrate (i.e., a filtrate having an absorbance of less than 0.100, when measured at the maximum visible wavelength of the dyes in the aqueous dye solution) was obtained. The recovered colored calcium phosphate product was then dried at 95° C. overnight to form a calcium phosphate colorant, which was then milled to less than about 25 μm.

A color intensity test was performed on the milled calcium phosphate colorant. Color intensity was measured with reflecting spectrometry using the Hunter Color equations. The Hunter Color equations define color using three opponent-color coordinates, L, $a_L$ and $b_L$. A zero value for $a_L$ and $b_L$ lies on the black-white axis, indicating a shade of gray. Positive values of $a_L$ denote redness and negative values of $a_L$ denote greenness. Positive values of $b_L$ denote yellowness and negative values of $b_L$ denote blueness.

The L scale ranges from 100, indicating white or light, to zero, indicating black or dark; therefore, more intensely colored substances have lower L values than lighter colored substances.

This Hunter Color test was conducted with a Gardner XL 835 colorimeter in which the Hunter Scale L, $a_L$, $b_L$ values of a smooth pressed disc of dyed dicalcium phosphate was measured. Specifically, 4 grams of the second dicalcium phosphate cake is pressed at 7000 psi (with the pressure being released soon after 7000 psi is reached) in a 1 inch die in a hydraulic press (Angstrom, Inc., Chicago, Ill., Angstrom model 4451-A.) The pressed disc surface must be smooth. The smooth disc surface is placed over the back port of the colorimeter and the L, $a_L$, $b_L$ values were obtained. The process was repeated for each of Examples 1–4. The values are set forth in Table II.

TABLE II

| Hunter Color Values | Example 1 | Example 2 | Example 3 | Example 4 |
| --- | --- | --- | --- | --- |
| L | 71.0 | 57.5 | 72.8 | 71.9 |
| $a_L$ | −13.6 | +1.7 | +26.8 | −21.3 |
| $b_L$ | −29.4 | −32.8 | +4.5 | −7.4 |

As can be seen from Table III, the Example 1 and Example 2 colorants containing blue dye have blue color intensities as indicated by the negative $b_L$ values. The Example 3 colorant containing red dyes exhibits a strong red color intensity as indicated by the positive $a_L$ value, and the Example 4 colorant containing a mixture of blue and yellow dyes exhibits a strong green color intensity as indicated by the negative $a_L$ value.

Screening tests were then conducted to determine the amount of bleeding of the calcium phosphate colorants in water. These screening tests were carried out by measuring the visible absorbance of an aqueous filtrate from the slurry of the second calcium phosphate colorant. Specifically, 1.0 gram of the calcium phosphate cake colorant placed in a 50 ml beaker containing a magnetic stir bar, along with 29 g deionized water. The beaker was placed on a magnetic stir plate and stirred for 10 min. The slurry was then filtered with vacuum on #42 Whatman filter paper (Whatman International Ltd., England). A UV/Visible spectrometer, (Perkin Elmer model Lambda 2) was zeroed with deionized water in both cells. One cuvette was filled with the filtrate obtained above and the reference cuvette was filled with deionized water. Absorbance was measured at the visible wavelength characteristic of the dye used, i.e. at 628 nm for the FD&C Blue No. 1 dye used in Examples 1 and 2; at 520 nm for the FD&C red No. 33 dye used in Example 3; and at 628 nm for the FD&C Blue No. 1 dye and at 410 nm for the FD&C Yellow No. 5 dye used in Example 4. The values obtained from the screening tests are set forth in Table III. It was determined experimentally that an absorbance reading of 0.100 or less indicates the colored calcium phosphate product has been washed sufficiently free of excess dye and should not bleed when incorporated into a consumer product.

TABLE III

| Screening test for Absorption at: | Example 1 | Example 2 | Example 3 | Example 4 |
|---|---|---|---|---|
| 628 nm | 0.086 | 0.094 | — | 0.094 |
| 520 nm | — | — | 0.046 | — |
| 410 nm | — | — | — | 0.083 |

All screening test values indicate that the products will have an extremely low level of bleeding when incorporated into a dentifrice formulation.

EXAMPLES 5–7

In Examples 5–7, calcium phosphate colorants were prepared according to the present invention. However, in contrast to Examples 1–4, in Examples 5–7 the aluminum hydroxide is generated, in situ, from acidic sulfate and basic carbonate reactants.

In this method, the first reactant, 800 g of a 12% aqueous solution of aluminum sulfate was added to the reactor vessel, then the second reactant, an 18% aqueous solution of sodium carbonate, was metered into the vessel at a rate of 7 ml/minute until the pH reached 5.9. The reactants were mixed together for 20 minutes under agitation. Next, 54 grams of calcium pyrophosphate was added and the resulting slurry was mixed for 15 minutes with agitation and filtered and washed to a conductivity of about 2000 μmhos. The recovered wetcake was reslurried with 150 g of water and 200 g of a 1% FD&C Blue No. 1 aqueous solution to form a slurry of colored calcium phosphate colorant and this slurry was then mixed for approximately 1 hour.

The slurry of colored calcium pyrophosphate was then filtered and oven dried at 105° C. overnight to produce a dried cake of dyed calcium pyrophosphate. The dried cake was then milled, re-slurried in 1000 ml of water and then filtered and washed to remove excess dye until a colorless filtrate (i.e., a filtrate having an absorbance of less than 0.100, tested at the maximum wavelength of the dye in the cake) was obtained. The recovered calcium pyrophosphate product was then dried at 95° C. overnight to form a calcium phosphate colorant and milled.

For Example 6, the identical method of preparation as disclosed above in relation to Example 5 was followed except that in Example 6 dicalcium phosphate dihydrate was substituted for the calcium pyrophosphate of Example 5, and in Example 6, FD&C Blue No. 2 was substituted for the FD&C Blue No. 1 of Example 5.

For Example 7, the identical method of preparation as disclosed above in relation to Example 6 was followed except that in Example 7 a mixture of 120 ml of FD&C Blue No. 1 dye and 80 ml of FD&C Red No. 33 dye was substituted for the FD&C blue No. 2 of Example 6. The mixture of blue and red dyes in Example 7 results in a purple colored dicalcium phosphate dihydrate colorant.

Color intensity and screening tests were conducted on the colorants of Examples 5–7, in an identical fashion as described above in relation to Examples 1–4. The values are set forth below in Table IV.

TABLE IV

|  | Example 5 | Example 6 | Example 7 |
|---|---|---|---|
| Hunter Color Intensity Values: |  |  |  |
| L | 56.5 | 69.9 | 64.5 |
| $a_L$ | −13.3 | +3.0 | −1.7 |
| $b_L$ | −25.2 | −35.4 | −26.8 |
| Screening Absorption tests: |  |  |  |
| At 628 nm | 0.047 | 0.062 | 0.046 |
| At 520 nm |  |  | 0.029 |

As can be seen from the data in Table IV above, all three examples had a strong blue color intensity with $b_L$ readings between about −25 and −35. Screening test results were all well below 0.1 absorbance (measured at the wavelength indicated in Table IV), indicating the color was fixed to the calcium phosphate products and therefore the colorants should not bleed when incorporated into a dentifrice formulation.

COMPARATIVE EXAMPLE 1

A calcium phosphate colorant was prepared that contained no aluminum hydroxide, so as to compare the performance of the calcium phosphate colorants prepared according to the present invention (i.e., those that contain aluminum hydroxide as a dye fixing agent) with prior art calcium phosphate colorants that contain a calcium phosphate base, but no aluminum hydroxide.

In comparative example 1, a calcium phosphate colorant was prepared as follows. A dicalcium phosphate dihydrate slurry containing 54 grams of dicalcium phosphate dihydrate was mixed with 75 g of water, and 100 ml of a 1% aqueous solution of FD&C No. 1 Blue dye for approximately 1 hour. The mixed slurry was then filtered without washing, oven dried at 105° C. and milled. The resulting milled powder was reslurried in water, washed until a colorless filtrate (i.e., a filtrate having an absorbance of less than 0.100 at 628 nm) appeared to indicate that the cake had been sufficiently washed. Then the washed cake was dried at 105° C. and milled.

The color intensity and screening test measurements were conducted in comparative example 1 in an identical fashion as described above with respect to Examples 1–7. The results are given in table V, below.

COMPARATIVE EXAMPLE 2

A precipitated calcium carbonate ("PCC") colorant containing aluminum hydroxide was prepared so as to compare the performance of the colorants prepared according to the present invention (i.e., those with dicalcium phosphate as a base) with prior art colorants that contain PCC particles as a base.

The PCC colorant was prepared as follows. A PCC slurry of 54 grams PCC in 400 g water was formed and 193 g of aluminum hydroxide gel prepared as in Example 1, above, was mixed with 100 g water and added to the PCC slurry at a rate of 20 ml/min. The product of the combined slurries was mixed for 15 minutes and filtered without washing to form a PCC wetcake. The resulting aluminum hydroxide coated PCC wetcake was then reslurried with 150 g water and 200 g of a 1% aqueous solution of FD&C No. 1 Blue dye, with the resulting mixture stirred for 1 hour. Thereafter, the slurry was filtered without washing and dried overnight at 105° C. The dried PCC was milled and washed until a colorless filtrate (i.e., a filtrate having an absorbance of less than 0.100 at 628 nm) appeared. This washed wetcake was dried at 95° C.

The color intensity and screening test measurements were conducted in comparative example 2 in an identical fashion as described above with respect to Examples 1–7. The results are given in table V, below.

TABLE V

|  | Comparative Example 1 | Comparative Example 2 |
|---|---|---|
| Hunter Color Intensity values: |  |  |
| L | 93.6 | 84.6 |
| $a_L$ | −2.10 | −4.20 |
| $b_L$ | −3.50 | −8.50 |
| Screening absorption test (@ 628 nm) | 0.056 | 0.065 |

It was established above with respect to Examples 1–7, that an acceptable blue dicalcium phosphate dihydrate colorant has an L value of less than about 75 and a $b_L$ value of less than about −20. As can be seen from the results in Table V, in comparative example 1 the blue dye is not fixed to the underlying dicalcium phosphate, and in fact the comparative example 1 product is nearly white (L=93.6), indicating that most of the dye was washed form the dicalcium phosphate dihydrate.

Similar conclusions may be made in regard to Comparative Example 2, as the results in Table V show that the blue dye was not fixed to the underlying calcium carbonate. Comparative Example 2 demonstrates that the dye material was not fixed to a non-phosphate calcium species (i.e., PCC), even when that species is coated with aluminum hydroxide gel. Since both comparative example products were essentially white, they have no value as colorants.

EXAMPLE 8

To demonstrate their efficacy in consumer products, the dicalcium phosphate dihydrate colorants of Examples 1 and 2 were incorporated as powders into three different striped toothpaste compositions. The striped toothpaste compositions were created by combining a white layer and three different blue gel layers. The white layer, which is set forth as sample 1 in table VII, is identical in each toothpaste composition. The blue gel layers in each of the toothpaste compositions, which are set forth as samples 2–4 in table V, are each nearly identical to the white layer, but each of them contains a different colorant additive. In the blue layer designated as sample 2 (below) the colorant additive is the dicalcium phosphate dihydrate colorant prepared according to Example 1, above. In sample 3 the colorant additive is the dicalcium phosphate dihydrate colorant of Example 2, above. In Sample 4, which is included for comparative purposes as representative of the prior art, the colorant is a conventional F&DC dye not fixed to any particular substrate.

Toothpaste samples 1–4 were prepared as follows. A first mixture was formed by combining the following components, in this specific order: glycerin, polyethylene glycol (CARBOWAX 600, from the Union Carbide Corporation, Danbury, Conn), carboxymethylcellulose (CMC-7MFX, from the Aqualon division of Hercules Corporation, Wilmington, Del.), and sorbitol. The mixture was stirred until the components dissolved. A second mixture was formed by combining the following components, in this specific order: water, saccharin, sodium monofluorophosphate (or sodium fluoride), and tetrasodium pyrophosphate, and stirred until the components dissolved. The first and second mixtures were then combined while stirring to form a premix. The premix was placed into a Ross mixer (model 130LDM, Charles Ross & Co., Haupeauge, N.Y.), silica thickener and silica abrasive added to the premix, and the premix agitated without vacuum at about 63 Hz. For toothpaste samples 2–4, the dye or colorant was then added while stirring. Then 30 inches of vacuum was drawn and each sample mixed for 15 minutes, and then sodium lauryl sulfate and flavor was added. The resulting slurry was stirred for 5 minutes at a reduced mixing speed (about 30 Hz).

Several toothpaste layers were formulated as follows, wherein the amounts are in grams:

TABLE VI

|  | Sample 1 (White layer) | Sample 2 (Colored gel layer) | Sample 3 (Colored gel layer) | Sample 4 (Colored prior art gel layer) |
|---|---|---|---|---|
| Glycerin, (99.5%) | 25.00 | 25.00 | 25.00 | 25.00 |
| Sorbitol, (70.0%) | 38.64 | 38.64 | 38.64 | 38.59 |
| Deionized water | 6.00 | 6.00 | 6.00 | 6.00 |
| Carbowax 600 | 3.000 | 3.000 | 3.000 | 3.00 |
| CMC-7MXF | 0.350 | 0.350 | 0.350 | 0.400 |
| Tetrasodium pyrophosphate | 0.500 | 0.500 | 0.500 | 0.500 |
| Sodium saccharin | 0.200 | 0.200 | 0.200 | 0.200 |
| Sodium monofluorophosphate | 0.760 | 0.760 | 0.760 | 0.760 |
| Zeodent ® 165 silica thickener | 4.20 | 4.20 | 4.20 | 4.50 |
| Zeodent ® 115 silica abrasive | 19.00 | 17.50 | 17.50 | 19.00 |
| Colorant prepared according to Example 1 | 0.00 | 2.00 | 0.00 | 0.00 |
| Colorant prepared according to Example 2 | 0.00 | 0.00 | 2.00 | 0.00 |
| 1% FD&C Blue No. 1 | 0.00 | 0.00 | 0.00 | 0.20 |
| $TiO_2$ | 0.50 | 0.00 | 0.00 | 0.00 |
| Sodium laurel sulfate | 1.20 | 1.20 | 1.20 | 1.20 |
| Flavor | 0.65 | 0.65 | 0.65 | 0.65 |

After samples 1–4 were prepared as above, the dye migration in three striped toothpastes made from these samples was tested as follows. Each of these striped toothpastes were made by use of a 10 cm³ syringe, of which the tip has been cut off so that the end opening is about ¼ inch in diameter, to deposit the toothpaste. A plexiglass microscope slide spacer (38×75 mm, 3 mm thick with a 24×47 mm open space) was centered onto a microscope slide, the slide sitting on a clear flat surface. A ribbon of colored gel toothpaste was squeezed from the aforementioned modified syringe and placed along one 24 mm side of the spacer opening, and a ribbon of opaque white toothpaste was similarly spaced along the other 24 mm side of the spacer. Another microscope slide was placed on top of the spacer and slowly and evenly pressure was applied, by hand, to force the two ribbons to meet in the center of the spacer, thereby removing excess air and excess toothpaste to form the striped layered toothpaste composition. Using these methods, three separate striped toothpaste compositions were made by combining the white toothpaste layer with each of blue gel samples 2, 3, and 4. Two slides were made for each of the striped toothpaste compositions.

Spectrometer measurements of the toothpaste sample were then made by holding the long side horizontally against the back port of a Gardner XL-835 colorimeter (previously calibrated) allowing light to pass through a part of the slide containing no air bubbles, while simultaneously covering the slide with the instrument's white calibration tile plate. Measurements of the L, $a_L$ and $b_L$ values for these samples were made initially after preparation and at 1 week, and 3 weeks for slides stored at room temperature (68° F.) and elevated temperature (120° F.). The Results are set forth in table VII, below:

TABLE VII

| | $b_L$ of Toothpaste 2 (Combination of Sample 2/white opaque layer) | $b_L$ of Toothpaste 3 (Combination of Sample 3/white opaque layer) | $b_L$ of Toothpaste 4 (Combination of Sample 4/white opaque layer) |
|---|---|---|---|
| At 24 hr. and 68° F. | +1.5 | +1.8 | −0.3 |
| 1 week, 68° F. | +1.5 | +1.6 | −0.3 |
| 3 weeks, 68° F. | +0.8 | +1.3 | −0.9 |
| Difference ($\Delta b_L$) | +0.7 | +0.5 | +0.6 |
| 24 hr., 120° F. | +1.6 | +1.9 | −0.10 |
| 1 week, 120° F. | +1.8 | +1.6 | −1.40 |
| 3 weeks, 120° F. | +2.9 | +3.0 | −2.80 |
| Difference ($\Delta b_L$) | +1.3 | +1.1 | −2.70 |

The degree of migration of dye from the blue layer to the white layer can be measured by the change in the $b_L$ value of the white layer. An increasingly negative $b_L$ value indicates that blue dye is migrating from the blue layer to the white layer (because negative values for $b_L$ indicate blueness). As can be seen from the data in Table VII, at elevated temperatures in toothpastes 2 and 3 (using the dicalcium phosphate dihydrate colorant prepared according to the present invention), there was no measurable migration of dye out of the blue layers and into the white opaque toothpaste layer. By contrast, at elevated temperatures in prior art toothpaste 4 there was significant migration of blue dye out of the blue layer and into the white opaque layer as evidenced by the significant decrease in the $b_L$ value. The white layers did generally experience a marginal yellowing (positive values for $b_L$ indicating yellowness), which occurs because the white layer yellows somewhat when subjected to elevated temperatures.

EXAMPLE 9

To further demonstrate their efficacy in consumer products, the dicalcium phosphate dihydrate colorants of Examples 1–4 were incorporated as powders into several different speckled toothpaste compositions.

Toothpaste samples 5–9 were prepared as follows. A first mixture was formed by combining the following components, in this specific order: glycerin, polyethylene glycol (CARBOWAX 600, from the Union Carbide Corporation, Danbury, Conn), carboxymethylcellulose (CMC-7MFX, from the Aqualon division of Hercules Corporation, Wilmington, Del.), and sorbitol and the mixture stirred until the components dissolved. A second mixture was formed by combining the following components, in this specific order: water, saccharin, sodium monofluorophosphate (or sodium fluoride), and tetrasodium pyrophosphate, and stirred until the components are dissolved. The first and second mixtures were then combined while stirring to form a premix. The premix was placed into a Ross mixer (model 130LDM, Charles Ross & Co., Haupeauge, N.Y.), and silica thickener and silica abrasive added to the premix and the premix agitated without vacuum at about 63 Hz. Then 30 inches of vacuum was drawn and each sample mixed for 15 minutes, and then sodium lauryl sulfate and flavor was added along with colorant speckles prepared according to the present invention (for toothpastes 5–8) or colored silica (for toothpaste 9), and the mixture stirred for 5 minutes at a reduced mixing speed (about 30 Hz).

The colorant speckles included in toothpastes 5–8 were formed from dicalcium phosphate dihydrate colorants prepared according to Examples 1–4. These speckles were made by pressing about 2.5–4.0 g of the dried and milled dicalcium phosphate dihydrate colorants at 7,000–8,000 psi on an Angstrom hydraulic press fitted with a 1 inch die. The pressed particles were then screened on sieves with granules between 250 and 425 μm being retained for incorporation into speckled toothpaste formulations 5–8, which are set forth in Table VIII, below.

The colored silica in toothpaste 9 was a control sample for comparative purposes in which the speckles were prepared from a mixture of silica powder and lake pigments. The control sample of colored speckles was prepared as follows: 15 g of Zeodent® 113 silica (available from J.M. Huber Corporation, Edison, N.J.) and 0.2 g of FD&C Blue No. 1 aluminum lake (available from Warner Jenkinson Inc., St. Louis, Mo.) were physically dry mixed together. This mixture, which has a $b_L$ value of −27.2, was then pressed at 7000 psi, and the resulting particles screened on sieves with granules between 250 and 425 μm being retained for incorporation into a speckled toothpaste formulation 9, set forth in Table VIII, below.

Several speckled toothpastes were formulated as follows, wherein the amounts are in grams:

TABLE VIII

| | Toothpaste 5 | Toothpaste 6 | Toothpaste 7 | Toothpaste 8 | Toothpaste 9 |
|---|---|---|---|---|---|
| Glycerin, (99.5%) | 25.00 | 25.00 | 25.00 | 25.00 | 25.00 |
| Sorbitol, (70.0%) | 38.64 | 38.64 | 38.64 | 38.64 | 38.59 |
| Deionized water | 6.00 | 6.00 | 6.00 | 6.00 | 6.00 |
| Carbowax 600 | 3.000 | 3.000 | 3.000 | 3.000 | 3.000 |
| CMC-7MXF | 0.350 | 0.350 | 0.350 | 0.350 | 0.400 |
| Tetrasodium pyrophosphate | 0.500 | 0.500 | 0.500 | 0.500 | 0.500 |
| Sodium saccharin | 0.200 | 0.200 | 0.200 | 0.200 | 0.200 |

TABLE VIII-continued

| | Toothpaste 5 | Toothpaste 6 | Toothpaste 7 | Toothpaste 8 | Toothpaste 9 |
|---|---|---|---|---|---|
| Sodium monofluorophosphate | 0.760 | 0.760 | 0.760 | 0.760 | 0.760 |
| Zeodent ® 165 silica thickener | 4.20 | 4.20 | 4.20 | 4.20 | 4.20 |
| Zeodent ® 115 silica abrasive | 19.00 | 19.00 | 19.00 | 19.00 | 19.00 |
| Colorant Prepared According to Example 1 | 0.50 | 0.00 | 0.00 | 0.00 | 0.00 |
| Colorant Prepared According to Example 2 | 0.00 | 0.50 | 0.00 | 0.00 | 0.00 |
| Colorant Prepared According to Example 3 | 0.00 | 0.00 | 0.50 | 0.00 | 0.00 |
| Colorant Prepared According to Example 4 | 0.00 | 0.00 | 0.00 | 0.50 | 0.00 |
| Control Colorant: Colored silica speckles | 0.00 | 0.00 | 0.00 | 0.00 | 0.50 |
| Sodium laurel sulfate | 1.20 | 1.20 | 1.20 | 1.20 | 1.20 |
| Flavor | 0.65 | 0.65 | 0.65 | 0.65 | 0.65 |

The dye migration in a speckled toothpaste was then tested as follows. A sample of the toothpaste was pushed out of the modified syringe described above in Example 8 by depressing the syringe plunger through a 100 mesh (150 μm) screen onto a sheet of weighing paper, which removed all the colored speckles from the toothpaste. A plexiglass microscope slide spacer (38×75 mm, 3 mm thick with a 24×47 mm open space) was filled with the screened toothpaste and another microscope slide placed on top of the spacer, and by slowly applying pressure, by hand, excess air and toothpaste was removed.

Spectrometer measurements of the toothpaste sample were then made by holding the long side horizontally against the back port of a Gardner XL-835 colorimeter (previously calibrated) allowing light to pass through a part of the slide containing no air bubbles, while simultaneously covering the slide with the instrument's white calibration tile plate. Measurements of the L, $a_L$ and $b_L$ values were made at 24 hours, 1 week, and 3 weeks. The Results are set forth in table IX, below:

TABLE IX

| | Toothpaste 5 ($b_L$) | Toothpaste 6 ($b_L$) | Toothpaste 7 ($a_L$) | Toothpaste 8 ($a_L$) | Toothpaste 9 ($a_L$) |
|---|---|---|---|---|---|
| 24 hours, at 68° F. | +2.3 | +1.0 | −1.0 | −3.2 | −11.4 |
| 1 week, at 68° F. | +1.9 | +0.9 | −0.6 | −3.3 | −15.5 |
| 3 weeks, at 68° F. | +2.2 | +0.9 | −0.4 | −3.5 | −16.3 |

Each entry in the table is the $a_L$ or $b_L$ value of the toothpaste, measured after the colored speckles have been removed as described above. The degree of migration of dye from the colored speckles into the toothpaste can be measured by the change in the $b_L$ value or $a_L$ value, as appropriate. As can be seen from the data in Table IX, in toothpastes 5–8, (which contained the dicalcium phosphate dihydrate colorant prepared according to the present invention), there was virtually no measurable migration of dye from the speckles and into the toothpaste. Specifically, as indicated by the $b_L$ values in toothpastes 5 and 6, there was virtually no sign of migration of dye from the blue speckles and into the toothpaste after either 24 hours or even 3 weeks. Similarly, the red speckles contained in toothpaste 7 and the green speckles contained in toothpaste 8, show negligible dye migration shown by the minimal differences in the 24 hour and 3 week $a_L$ values from the base toothpaste. Toothpaste 9 containing speckles prepared according to the prior art showed high levels of bleeding.

EXAMPLE 10

To further demonstrate their efficacy in consumer products other than toothpastes and dentifrices, a dicalcium phosphate dihydrate colorant of the present invention was incorporated into a cosmetic Exfoliating Facial Scrub.

This scrub composition was prepared by adding water to a mixing vessel followed by the addition of methyl paraben and Germall II and the resultant water phase was mixed and heated to 70° C. Thereafter, mineral oil was added to another vessel followed by Ritachol, cetyl alcohol and propyl paraben and this oil phase was also mixed and heated to 70° C. The oil phase was added to the water phase and the combination was homogenized. The homogenized mixture was cooled to 40° C., then perfume and Flocare were added. Thereafter, granules of the dicalcium phosphate dihydrate colorant of Example 1 were stirred in with energy sufficient to disperse, but not to break apart the granules. The resultant exfoliating facial scrub was cooled to room temperature.

The composition of the scrub was as follows, wherein the amounts are in weight percentages:

TABLE X

| Ingredient | Ingredient composed of: | Wt % |
|---|---|---|
| water | Water | 78.6 |
| Nipagin (Nipa) | Methyl paraben | 0.15 |
| Germall 115 (Sutton) | Imidazolidinyl urea | 0.3 |
| mineral oil | Paraffinum Liquidum | 12 |
| Ritachol 1000 (RITA) | Cetearyl alcohol Polysorbate 60 PEG 150 stearate Steareth 20 | 4 |
| Rita CA (RITA) | Cetyl alcohol | 2 |
| Nipasol (Nipa) | Propyl paraben | 0.1 |
| perfume | | 0.15 |
| Flocare ET 100 (SNF) | Sodium polyacrylate Ethylhexyl stearate Trideceth-6 | 0.20 |

TABLE X-continued

| Ingredient | Ingredient composed of: | Wt % |
|---|---|---|
| Granules of colorant prepared according to Example 1 | | 2.5 |

No dye migration from the dicalcium phosphate dihydrate colorant granules was detected when the scrub was stored at room temperature for two months.

EXAMPLE 11

The colored dicalcium phosphate dihydrate speckles of Example 1 were incorporated into a pearlescent shower gel formulation to impart a pleasing speckled appearance to the product. Ingredients were mixed together in a vessel with low shear to prevent aeration. Citric acid was added to the shower gel to adjust the gel to the desired pH and viscosity levels. The composition was as follows:

TABLE XI

| Ingredient | Ingredient composed of: | Source | Wt % |
|---|---|---|---|
| Water | | | 51.52 |
| Structure Plus | Acrylates Aminoacrylates C10–30 Alkyl PEG-20 Itaconate Copolymer | National Starch | 13.00 |
| Perfume | | | 0.20 |
| Solubilisant LRI | PPG-24-Buteth-26 PEG-40 hydrogenated castor oil | LCW/Warner Jenkinson | 0.40 |
| Texapon NSO/IS | Sodium lauryl sulfate | Cognis | 30.00 |
| Euxyl K 100 | Benzyl alcohol Methychlorois othiazolinone Methylisothiaz olinone | S&MI | 0.08 |
| Euperlan PK 900 | Glycol distearate Sodium lauryl sulfate Cocamide MEA Laureth 10 | Cognis | 3.00 |
| Timica Sparkle | Mica Titanium dioxide | Engelhard | 0.30 |
| Ex. 1 colored granules | Dicalcium phosphate dihydrate and FD&C Blue No. 1 | | 2.5 |
| Citric Acid | | | qs |

No dye migration from dicalcium phosphate dihydrate colorant granules was detected when the shower gel was stored at room temperature for two months.

EXAMPLE 12

The inventive colored speckles were incorporated into a cosmetic after-shave balm according to the following procedure. A "pre-mix" of colored speckles was prepared from 20 weight per cent Example 1 colored dicalcium phosphate dihydrate speckles and 80 weight per cent C12–C14 alkyl benzoate. A portion of the pre-mix was combined with the rest of the ingredients listed in Table XII below.

TABLE XII

| Ingredient | Ingredient composed of: | Source | Wt % |
|---|---|---|---|
| Finsolv TN | C12–15 alkyl benzoate | Finetex | 10 |
| Olivem 700 | PEG-4 Olivate | B&T | 2 |
| Ritachol 1000 | Cetearyl alcohol | RITA | 3 |
| | Polysorbate 60 PEG-150 stearate Steareth 20 | | |
| Flocare ET 100 | Sodium polyacrylate Ehtylhexyl stearate Trideceth-6 | SNF | 0.3 |
| Ritapan D | D-panthenol | RITA | 0.1 |
| Aloe Vera | Aloe vera | | 0.5 |
| Pelemol G7A | Glycereth-7 triacetate | Phoenix | 2 |
| Nipagin M | Methyl paraben | Nipa | 0.15 |
| Nipasol M | Propyl paraben | Nipa | 0.10 |
| Germall 115 | Imidazolindinyl urea | Sutton | 0.3 |
| Perfume | | | 0.15 |
| Colored speckle pre-mix | | | 0.07 |
| Water | | | qs |

No dye migration from dicalcium phosphate dihydrate colorant granules was detected when the after shave balm was stored at room temperature for two months.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method of forming a calcium phosphate colorant comprising the steps of:
    a) providing a calcium phosphate slurry comprising calcium phosphate particles;
    b) mixing the aluminum hydroxide with the calcium phosphate slurry to form a premix, thereby depositing aluminum hydroxide onto the calcium phosphate particles; and
    c) applying a dye to the calcium phosphate particles, wherein the dye is fixed to the calcium phosphate particles by aluminum hydroxide.

2. The method according to claim 1 further comprising the steps of:
    d) drying the calcium phosphate slurry to obtain a calcium phosphate cake;
    e) mixing the dried calcium phosphate slurry with water to obtain a second calcium phosphate slurry; and
    f) filtering and washing the second calcium phosphate slurry to obtain a filter cake.

3. The method according to claim 2, further comprising the step of g) drying the filter cake to obtain a calcium phosphate colorant.

4. The method according to claim 3, wherein following step g) the moisture level in the calcium phosphate colorant is less than about 10%, by weight.

5. The method of claim 3, wherein following step g), the method further comprises the step of h) milling the calcium phosphate colorant to obtain calcium phosphate particles.

6. The method of claim 2, wherein following step f) the filter cake has an absorption of less than about 0.100.

7. The method of claim 3, wherein the drying step d) occurs at a temperature of $T_1$, the re-drying step g) occurs at a temperature of $T_2$, and $T_1 \geq T_2$.

8. The method of claim 4, wherein the dried calcium phosphate slurry obtained in step d) has a moisture level of $M_1$, the calcium phosphate colorant has a moisture level of $M_2$, and $M_2 \geq M_1$.

9. The method of claim 1, wherein step b) occurs in a vessel and before the aluminum hydroxide is deposited on the particles, the aluminum hydroxide is formed by reacting aluminum sulfate and sodium carbonate, in situ, in the vessel.

10. The method of claim 1, wherein the calcium phosphate is selected from the group consisting of dicalcium phosphate, dicalcium phosphate dihydrate, calcium pyrophosphate and tricalcium phosphate.

11. A dentifrice comprising the calcium phosphate colorant prepared according to the method of claim 1.

12. A cosmetic product comprising the calcium phosphate colorant prepared according to the method of claim 1.

13. A food product comprising the calcium phosphate colorant prepared according to the method of claim 1.

14. The method according to claim 5 further comprising the step of i) granulating the calcium phosphate particles.

15. A calcium phosphate colorant resistant to dye migration comprising calcium phosphate particles, a dye, and aluminum hydroxide.

16. The calcium phosphate colorant of claim 15, wherein the particles are coated with a dye and the dye is fixed to the particles by the aluminum hydroxide.

17. The calcium phosphate colorant of claim 15, wherein the colorant has a moisture level of less than about 10% by weight.

18. The calcium phosphate colorant of claim 15, wherein the dye is selected from the group consisting of FD&C dyes and D&C dyes.

19. The calcium phosphate colorant of claim 15 wherein the calcium phosphate is in particulate form and has a median particle size of less than about 25 microns.

20. The calcium phosphate colorant of claim 15 wherein the calcium phosphate is in granular form and has a particle size of from about 180 to about 600 microns.

21. A dentifrice comprising the calcium phosphate colorant of claim 15.

22. A cosmetic product comprising the calcium phosphate colorant of claim 15.

23. A food product comprising the calcium phosphate colorant of claim 15.

24. A method of forming a calcium phosphate colorant comprising the steps of:
 a) providing a calcium phosphate slurry comprising calcium phosphate particles;
 b) mixing the aluminum hydroxide with the calcium phosphate slurry to form a premix, thereby depositing aluminum hydroxide onto the calcium phosphate particles;
 c) applying a dye to the calcium phosphate particles;
 d) drying the calcium phosphate slurry to obtain a calcium phosphate cake;
 e) mixing the dried calcium phosphate slurry with water to obtain a second calcium phosphate slurry; and
 f) filtering and washing the second calcium phosphate slurry to obtain a filter cake, wherein the dye is fixed to the calcium phosphate particles by aluminum hydroxide.

25. The method according to claim 24, further comprising the step of g) drying the filter cake to obtain a calcium phosphate colorant.

26. The method according to claim 25, wherein following step g) the moisture level in the calcium phosphate colorant is less than about 10%, by weight.

27. The method of claim 25, wherein following step g), the method further comprises the step of h) milling the calcium phosphate colorant to obtain calcium phosphate particles.

28. The method of claim 24, wherein following step f) the filter cake has an absorption of less than about 0.100.

29. The method of claim 25, wherein the drying step d) occurs at a temperature of $T_1$, the re-drying step g) occurs at a temperature of $T_2$, and $T_1 \geq T_2$.

30. The method of claim 25, wherein the dried calcium phosphate slurry obtained in step d) has a moisture level of $M_1$, the calcium phosphate colorant has a moisture level of $M_2$, and $M_2 \geq M_1$.

* * * * *